(12) United States Patent
Omura

(10) Patent No.: US 8,043,638 B2
(45) Date of Patent: Oct. 25, 2011

(54) MUTANT ILV5 GENE AND USE THEREOF

(75) Inventor: Fumihiko Omura, Osaka (JP)

(73) Assignee: Suntory Holdings Limited, Osaka (JP)

( * ) Notice: Subject to any disclaimer, the term of this patent is extended or adjusted under 35 U.S.C. 154(b) by 328 days.

(21) Appl. No.: 12/303,266

(22) PCT Filed: Dec. 17, 2007

(86) PCT No.: PCT/JP2007/074620
§ 371 (c)(1),
(2), (4) Date: Dec. 3, 2008

(87) PCT Pub. No.: WO2009/078108
PCT Pub. Date: Jun. 25, 2009

(65) Prior Publication Data
US 2011/0027414 A1    Feb. 3, 2011

(51) Int. Cl.
*C12C 11/00* (2006.01)
*C12H 1/14* (2006.01)
*C12N 1/00* (2006.01)
*C12N 15/00* (2006.01)
*C12N 9/90* (2006.01)
*C12P 21/06* (2006.01)
*C07K 1/00* (2006.01)
*C07H 21/04* (2006.01)

(52) U.S. Cl. ......... 426/11; 426/16; 426/592; 435/254.2; 435/254.11; 435/320.1; 435/69.1; 435/233; 530/350; 536/23.74; 536/23.1; 536/23.2

(58) Field of Classification Search .................... 426/11, 426/16, 592; 435/254.2, 254.11, 320.1, 69.1, 435/233; 530/350; 536/23.74, 23.1, 23.2
See application file for complete search history.

(56) References Cited

FOREIGN PATENT DOCUMENTS
WO        2007/020993 A1    2/2007

OTHER PUBLICATIONS

Kozak M., Structural features in eukaryotic mRNAs that modulate the initiation of translation. J. Biol. Chem., 1991, vol. 266 (30): 19867-19870.*
Kozak M., Initiation of translation in prokaryotes and eukaryotes. Gene, 1999, vol. 234: 187-208.*
Villa et al., "Control of Vicinal Diketone Production by Brewer's Yeast. I. Effects of *ILV5* and *ILV3* Gene Amplification on Vicinal Diketone Production and *ILV* Enzyme Activity" J. Am. Soc. Brew. Chem., vol. 53, No. 2, pp. 49-53, 1995.
Petersen et al., "The ILV5 Gene of *Saccharomyces cervisiae* is Highly Expressed" Nucleic Acids Res., vol. 14, No. 24, pp. 9631-9651, 1986.
Xie et al., "Cloning and Molecular Analysis of Two Different *ILV5* Genes from a Brewing Strain of *Saccharomyces cerevisiae*" Current Genetics, vol. 26, pp. 398-402, 1994.
Japanese Office Action that issued with respect to patent family member Japanese Patent Application No. 2008-553415, dated Jan. 26, 2010.
Dillemans Met al. (1987), J AM Soc. Brew. Chem. 45, pp. 81-84.
Kassow A (1992), Metabolic effects of deleting the region encoding the transit peptide in *Saccharomyces cerevisiae* ILV5. PhD thesis, University of Copenhagen.
Gjermansen et al., (1998), Journal of Basic Microbiology, Berlin, De, vol. 28, No. 3, pp. 175-183.
Omura Fumihiko, (2008), Applied Microbiology and Biotechnology, vol. 78, No. 3, pp. 503-513.
Villanueba, K.D., et al., (1990), J.Am. Soc. Brew. Chem., 48, pp. 111-114.

* cited by examiner

*Primary Examiner* — Ganapathirama Raghu
(74) *Attorney, Agent, or Firm* — Greenblum & Bernstein, P.L.C.

(57) ABSTRACT

The present invention relates to a mutant acetohydroxy-acid reductoisomerase gene (mutant ILV5 gene) and use thereof, in particular, a brewery yeast for producing alcoholic beverages with superior flavor, alcoholic beverages produced with said yeast, and a method for producing said beverages. According to the method for producing alcoholic beverages of the present invention, because of reduction of the production of VDKs, especially DA, which are responsible for off-flavors in products, alcoholic beverages with superior flavor can be produced.

12 Claims, 6 Drawing Sheets

SEQUENCE LISTING

```
<160> NUMBER OF SEQ ID NOS: 18

<210> SEQ ID NO 1
<211> LENGTH: 1053
<212> TYPE: DNA
<213> ORGANISM: Saccharomyces sp.
<220> FEATURE:
<221> NAME/KEY: CDS
<222> LOCATION: (1)..(1050)
<223> OTHER INFORMATION: Mutant Ilv5 protein

<400> SEQUENCE: 1 atg ggt ttg aag caa atc aac ttc ggt ggt act gtt gaa acc gtc tac    48
Met Gly Leu Lys Gln Ile Asn Phe Gly Gly Thr Val Glu Thr Val Tyr
1               5                   10                  15 gaa aga gct gac tgg cca aga gaa aag ttg ttg gac tac ttc aag aac    96
Glu Arg Ala Asp Trp Pro Arg Glu Lys Leu Leu Asp Tyr Phe Lys Asn
            20                  25                  30 gac act ttt gct ttg atc ggt tac ggt tcc caa ggt tac ggt caa ggt   144
Asp Thr Phe Ala Leu Ile Gly Tyr Gly Ser Gln Gly Tyr Gly Gln Gly
        35                  40                  45 ttg aac ttg aga gac aac ggt ttg aac gtt atc att ggt gtc cgt aaa   192
Leu Asn Leu Arg Asp Asn Gly Leu Asn Val Ile Ile Gly Val Arg Lys
    50                  55                  60
```

```
gat ggt gct tct tgg aag gct gcc atc gaa gac ggt tgg gtt cca ggc      240
Asp Gly Ala Ser Trp Lys Ala Ala Ile Glu Asp Gly Trp Val Pro Gly
 65                  70                  75                  80 aag aac ttg ttc act gtt gaa gat gct atc aag aga ggt agt tac gtt      288
Lys Asn Leu Phe Thr Val Glu Asp Ala Ile Lys Arg Gly Ser Tyr Val
                 85                  90                  95 atg aac ttg ttg tcc gat gcc gct caa tca gaa acc tgg cct gct atc      336
Met Asn Leu Leu Ser Asp Ala Ala Gln Ser Glu Thr Trp Pro Ala Ile
            100                 105                 110 aag cca ttg ttg acc aag ggt aag act ttg tac ttc tcc cac ggt ttc      384
Lys Pro Leu Leu Thr Lys Gly Lys Thr Leu Tyr Phe Ser His Gly Phe
        115                 120                 125 tcc cca gtc ttc aag gac ttg act cac gtt gaa cca cca aag gac tta      432
Ser Pro Val Phe Lys Asp Leu Thr His Val Glu Pro Pro Lys Asp Leu
    130                 135                 140 gat gtt atc ttg gtt gct cca aag ggt tcc ggt aga act gtc aga tct      480
Asp Val Ile Leu Val Ala Pro Lys Gly Ser Gly Arg Thr Val Arg Ser
145                 150                 155                 160 ttg ttc aag gaa ggt cgt ggt att aac tct tct tac gcc gtc tgg aac      528
Leu Phe Lys Glu Gly Arg Gly Ile Asn Ser Ser Tyr Ala Val Trp Asn
                165                 170                 175 gat gtc acc ggt aag gct cac gaa aag gcc caa gct ttg gcc gtt gcc      576
Asp Val Thr Gly Lys Ala His Glu Lys Ala Gln Ala Leu Ala Val Ala
            180                 185                 190 att ggt tcc ggt tac gtt tac caa acc act ttc gaa aga gaa gtc aac      624
Ile Gly Ser Gly Tyr Val Tyr Gln Thr Thr Phe Glu Arg Glu Val Asn
        195                 200                 205 tct gac ttg tac ggt gaa aga ggt tgt tta atg ggt ggt atc cac ggt      672
Ser Asp Leu Tyr Gly Glu Arg Gly Cys Leu Met Gly Gly Ile His Gly
    210                 215                 220 atg ttc ttg gct caa tac gac gtc ttg aga gaa aac ggt cac tcc cca      720
Met Phe Leu Ala Gln Tyr Asp Val Leu Arg Glu Asn Gly His Ser Pro
225                 230                 235                 240 tct gaa gct ttc aac gaa acc gtc gaa gaa gct acc caa tct cta tac      768
Ser Glu Ala Phe Asn Glu Thr Val Glu Glu Ala Thr Gln Ser Leu Tyr
                245                 250                 255 cca ttg atc ggt aag tac ggt atg gat tac atg tac gat gct tgt tcc      816
Pro Leu Ile Gly Lys Tyr Gly Met Asp Tyr Met Tyr Asp Ala Cys Ser
            260                 265                 270 acc acc gcc aga aga ggt gct ttg gac tgg tac cca atc ttc aag aat      864
Thr Thr Ala Arg Arg Gly Ala Leu Asp Trp Tyr Pro Ile Phe Lys Asn
        275                 280                 285 gct ttg aag cct gtt ttc caa gac ttg tac gaa tct acc aag aac ggt      912
Ala Leu Lys Pro Val Phe Gln Asp Leu Tyr Glu Ser Thr Lys Asn Gly
    290                 295                 300 acc gaa acc aag aga tct ttg gaa ttc aac tct caa cct gac tac aga      960
Thr Glu Thr Lys Arg Ser Leu Glu Phe Asn Ser Gln Pro Asp Tyr Arg
305                 310                 315                 320 gaa aag cta gaa aag gaa tta gac acc atc aga aac atg gaa atc tgg     1008
Glu Lys Leu Glu Lys Glu Leu Asp Thr Ile Arg Asn Met Glu Ile Trp
                325                 330                 335 aag gtt ggt aag gaa gtc aga aag ttg aga cca gaa aac caa taa         1053
Lys Val Gly Lys Glu Val Arg Lys Leu Arg Pro Glu Asn Gln
            340                 345                 350

<210> SEQ ID NO 2
<211> LENGTH: 350
<212> TYPE: PRT
<213> ORGANISM: Saccharomyces sp.
```

<400> SEQUENCE: 2

| | | | | | | | | | | | | | | |
|---|---|---|---|---|---|---|---|---|---|---|---|---|---|---|
| Met | Gly | Leu | Lys | Gln | Ile | Asn | Phe | Gly | Thr | Val | Glu | Thr | Val | Tyr |
| 1 | | | | 5 | | | | | 10 | | | | | 15 |
| Glu | Arg | Ala | Asp | Trp | Pro | Arg | Glu | Lys | Leu | Leu | Asp | Tyr | Phe | Lys | Asn |
| | | | 20 | | | | | 25 | | | | | 30 | | |
| Asp | Thr | Phe | Ala | Leu | Ile | Gly | Tyr | Gly | Ser | Gln | Gly | Tyr | Gly | Gln | Gly |
| | | | 35 | | | | | 40 | | | | | 45 | | |
| Leu | Asn | Leu | Arg | Asp | Asn | Gly | Leu | Asn | Val | Ile | Ile | Gly | Val | Arg | Lys |
| | 50 | | | | | 55 | | | | | 60 | | | | |
| Asp | Gly | Ala | Ser | Trp | Lys | Ala | Ala | Ile | Glu | Asp | Gly | Trp | Val | Pro | Gly |
| 65 | | | | | 70 | | | | | 75 | | | | | 80 |
| Lys | Asn | Leu | Phe | Thr | Val | Glu | Asp | Ala | Ile | Lys | Arg | Gly | Ser | Tyr | Val |
| | | | | 85 | | | | | 90 | | | | | 95 | |
| Met | Asn | Leu | Leu | Ser | Asp | Ala | Ala | Gln | Ser | Glu | Thr | Trp | Pro | Ala | Ile |
| | | | 100 | | | | | 105 | | | | | 110 | | |
| Lys | Pro | Leu | Leu | Thr | Lys | Gly | Lys | Thr | Leu | Tyr | Phe | Ser | His | Gly | Phe |
| | | | 115 | | | | | 120 | | | | | 125 | | |
| Ser | Pro | Val | Phe | Lys | Asp | Leu | Thr | His | Val | Glu | Pro | Pro | Lys | Asp | Leu |
| | 130 | | | | | 135 | | | | | 140 | | | | |
| Asp | Val | Ile | Leu | Val | Ala | Pro | Lys | Gly | Ser | Gly | Arg | Thr | Val | Arg | Ser |
| 145 | | | | | 150 | | | | | 155 | | | | | 160 |
| Leu | Phe | Lys | Glu | Gly | Arg | Gly | Ile | Asn | Ser | Ser | Tyr | Ala | Val | Trp | Asn |
| | | | | 165 | | | | | 170 | | | | | 175 | |
| Asp | Val | Thr | Gly | Lys | Ala | His | Glu | Lys | Ala | Gln | Ala | Leu | Ala | Val | Ala |
| | | | 180 | | | | | 185 | | | | | 190 | | |
| Ile | Gly | Ser | Gly | Tyr | Val | Tyr | Gln | Thr | Thr | Phe | Glu | Arg | Glu | Val | Asn |
| | | | 195 | | | | | 200 | | | | | 205 | | |
| Ser | Asp | Leu | Tyr | Gly | Glu | Arg | Gly | Cys | Leu | Met | Gly | Gly | Ile | His | Gly |
| | 210 | | | | | 215 | | | | | 220 | | | | |
| Met | Phe | Leu | Ala | Gln | Tyr | Asp | Val | Leu | Arg | Glu | Asn | Gly | His | Ser | Pro |
| 225 | | | | | 230 | | | | | 235 | | | | | 240 |
| Ser | Glu | Ala | Phe | Asn | Glu | Thr | Val | Glu | Glu | Ala | Thr | Gln | Ser | Leu | Tyr |
| | | | | 245 | | | | | 250 | | | | | 255 | |
| Pro | Leu | Ile | Gly | Lys | Tyr | Gly | Met | Asp | Tyr | Met | Tyr | Asp | Ala | Cys | Ser |
| | | | 260 | | | | | 265 | | | | | 270 | | |
| Thr | Thr | Ala | Arg | Arg | Gly | Ala | Leu | Asp | Trp | Tyr | Pro | Ile | Phe | Lys | Asn |
| | | | 275 | | | | | 280 | | | | | 285 | | |
| Ala | Leu | Lys | Pro | Val | Phe | Gln | Asp | Leu | Tyr | Glu | Ser | Thr | Lys | Asn | Gly |
| | 290 | | | | | 295 | | | | | 300 | | | | |
| Thr | Glu | Thr | Lys | Arg | Ser | Leu | Glu | Phe | Asn | Ser | Gln | Pro | Asp | Tyr | Arg |
| 305 | | | | | 310 | | | | | 315 | | | | | 320 |
| Glu | Lys | Leu | Glu | Lys | Glu | Leu | Asp | Thr | Ile | Arg | Asn | Met | Glu | Ile | Trp |
| | | | | 325 | | | | | 330 | | | | | 335 | |
| Lys | Val | Gly | Lys | Glu | Val | Arg | Lys | Leu | Arg | Pro | Glu | Asn | Gln | | |
| | | | 340 | | | | | 345 | | | | | 350 | | |

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gagctcatgt tgagaactca agccgccaga ttgatctgca          40

```
<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttggttttct ggtctcaact ttctgacttc ctta                              34

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cagaaagttg agaccagaaa accaaatgag taaaggagaa gaact                  45

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatcccagt gtgatggata tctgcagaat tcccggggta ccttatttgt             50

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagctcatgg ctaagagaac ctttgctttg gccacc                            36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagctcatgc cagctgcccg tttcgttaag ccaatg                            36

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagctcatgc caatgatcac tacccgtggt ttgaag                            36
```

```
<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagctcatgg gtttgaagca aatcaacttc ggtggt                                 36

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gagctcatgg gtggtactgt tgaaaccgtc tacgaa                                 36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagctcatgc aagagaaaa gttgttggac tacttc                                  36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagctcatgg gttacggttc ccaaggttac ggtcaa                                 36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagctcatgg gtttgaacgt tatcattggt gtccgt                                 36

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
taccggtgac atcgttccag acggcgt                                           27
```

```
<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
accggtaagg ctcacgaaaa ggcccaagct                                          30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcgacttat tggttttctg gtctcaactt                                          30

<210> SEQ ID NO 18
<211> LENGTH: 122
<212> TYPE: PRT
<213> ORGANISM: Saccharomyces sp.

<400> SEQUENCE: 18

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp
            115                 120
```

US 8,043,638 B2

MUTANT ILV5 GENE AND USE THEREOF

SEQUENCE LISTING

The instant application contains a Sequence Listing which has been submitted in ASCII format via EFS-Web and is hereby incorporated by reference in its entirety. Said ASCII copy, created on Sep. 30, 2010, is named P35607.txt and is 12,991 bytes in size.

TECHNICAL FIELD

The present invention relates to a mutant acetohydroxyacid reductoisomerase gene (mutant ILV5 gene) and use thereof, in particular, a brewery yeast for producing alcoholic beverages with superior flavor, alcoholic beverages produced with said yeast, and a method for producing said beverages.

BACKGROUND ART

The lager beer fermentation consists of two fermentation steps: the primary fermentation for production of ethanol and flavor compounds, and the second fermentation (or lagering period) for maturation of the beer flavors. During the first fermentation, yeast cells produce α-aceto-α-hydroxybutyrate and α-acetolactate, which are intermediates for synthesis of isoleucine and valine, respectively. Some part of these acetohydroxy acids diffuses out of the cells, and turns into two vicinal diketones (VDK), 2,3-pentandione and diacetyl, respectively, by a non-enzymatic oxidative decarboxylation in the beer (see FIG. 1). VDK gives a butter-like unpleasant flavor, and the threshold for 2,3-pentandione and diacetyl are 0.9 and 0.15 mg/L, respectively (Meilgaard 1975; the details of the cited references will be described at the end of the specification).

Spontaneous decarboxylation of α-acetolactate is the rate-limiting step of diacetyl formation. The amount of VDK is reduced to acceptable levels during the lagering period. A reduction of the time needed for beer maturation may be achieved by use of a brewing yeast strain that produces less VDKs. Acetohydroxyacid synthase (Ilv2p/Ilv6p), acetohydroxyacid reductoisomerase (Ilv5p), dihydroxy-acid dehydratase (Ilv3p), and branched-chain amino acid aminotransferase (Bat1p)/transaminase (Bat2p) catalyze two homologous reactions for synthesis of isoleucine and valine.

There are two distinct approaches for the construction of yeast strains with lower VDK productions: an inactivation of acetohydroxyacid synthase and an enhancement of the acetohydroxyacid reductoisomerase activity. Down regulation with anti-sense RNA of ILV2 gene encoding the catalytic subunit of acetohydroxyacid synthase decreases the enzymatic activity by more than 80%, and consequently reduces the diacetyl level at the fermentation mid-point by 40% (Vakeria et al. 1991).

On the other hand, the number of ILV5 gene encoding acetohydroxyacid reductoisomerase largely influences the VDK production. Yeast cells transformed with multicopy vectors carrying ILV5 show a five to ten-fold increase in the reductoisomerase activity and a concomitant decrease of diacetyl production by 50-60% compared to the control strain (Dillemans et al. 1987; Gjermansen et al. 1988). It is known that the enzymes involved in the synthesis of isoleucine and valine are located in the mitochondrial matrix (Ryan and Kohlhaw 1974). The mitochondria consist of two aqueous chambers (intermembrane and matrix) and two membranes (outer and inner membranes) (Wiedemann et al. 2003; Koehler 2004).

Since the mitochondria synthesize only eight stable proteins encoded by the mitochondrial DNA, most of the up to 1,000 mitochondrial proteins are encoded by the nuclear genome, synthesized in the cytoplasm on free ribosomes as precursor proteins, and then transported into or across mitochondrial membranes with the aid of protein assembries known as TOM and TIM (translocases of outer and inner mitochondrial membranes, respectively (Endo et al. 2003; Truscot et al. 2003). The Ilv2p and Ilv5p are synthesized as precursor proteins in the cytoplasm, and then are imported into the mitochondrial matrix via TOM and TIM23 translocases.

The N-terminal presequence is cleaved off by a mitochondrial specific processing peptidase during translocation to the mitochondrial matrix (Gakh et al. 2002). The N-terminal 47 residues have been identified as Ilv5p cleavable presequence (Kassow 1992). Kassow describes that an ILV5 gene deleted in the region encoding the transit peptide was constructed, and the construct seems to have an effect on the diacetyl production level.

As commonly observed in typical mitochondrial targeting presequences, Ilv5p presequence is rich in positive charge, and its cleavage site is preceded by an arginine at the position −2 (von Heijne et al. 1989; Gakh et al. 2002). Ilv5p is known as a bifunctional protein that acts in mitochondrial DNA stability as well as in the biosynthesis of branched-chain amino acids (Zelenaya-Troitskaya et al. 1995). Mitochondrial DNA is inherited as a protein-DNA complex (the nucleoid). Together with other factors, Ilv5p maintains a stoichiometry between the mitochondrial DNA and the nucleoids by parsing the mitochondrial DNA into individual nucleoid in response to amino acid starvation (MacAlpine et al. 2000). The enzymatic function in branched-chain amino acid synthesis and the function for the mitochondrial DNA stability of Ilv5p can be separated by mutational approaches (Bateman et al. 2002). The enzymatic mutations map to conserved internal domains that are important for substrate and cofactor binding, whereas the mutations concerning the function for mitochondrial DNA stability map to the C-terminal region on the surface of Ilv5p. It is known that respiration-deficient (rho$^-$) yeast produces elevated levels of VDK (Ernandes et al. 1993). This leads to a hypothesis that this is because acetohydroxyacid synthase (Ilv2p) does not properly localize in the mitochondria when it is "sick" (rho$^-$), but rather tends to localize in the cytoplasm, where α-acetolactate is easily formed from cytoplasmic pyruvate.

Based on this idea, expression of a cytoplasmic Ilv5p has been explored in order to metabolize the cytoplasmically formed α-acetolactate (Kassow 1992). The cytoplasmic Ilv5p without N-terminal 47 residues complements auxotrophy of isoleucine but not of valine in an Ilv5Δ strain, indicating that a small portion of the truncated Ilv5p still localizes in the mitochondria supporting isoleucine synthesis.

DISCLOSURE OF INVENTION

Under the circumstances described above, there were demands for developing a method for producing alcoholic beverages capable of reducing the production of VDKs (vicinal diketones), especially DA (diacetyl).

To solve the problems described above, the present inventors made exhaustive studies, and, as a result, found that expression of a cytoplasmic Ilv5p with a deletion of the N-terminal 46 residues in lager brewing yeast was effective in lowering VDK production without major alterations in the resultant beer quality.

Thus, the present invention relates to a specific mutant Ilv5 gene, to a protein encoded by said gene, to a transformed yeast in which the expression of said gene is controlled, to a method for controlling the level of VDKs, especially the level of DA, in a product by using a yeast in which the expression of said gene is controlled. More specifically, the present invention provides the following polynucleotides, a vector comprising said polynucleotide, a transformed yeast introduced with said vector, a method for producing alcoholic beverages by using said transformed yeast, and the like.

(1) A polynucleotide selected from the group consisting of
(a) a polynucleotide consisting of the nucleotide sequence of SEQ ID NO:1;
(b) a polynucleotide encoding a protein consisting of the amino acid sequence of SEQ ID NO:2; and
(c) a polynucleotide encoding a protein consisting of the amino acid sequence of SEQ ID NO:2 with one to 15 amino acids thereof being deleted, substituted, inserted and/or added, and having an acetohydroxy-acid reductoisomerase activity, with proviso that the addition and/or deletion does not occur at the N-terminus.

(2) The polynucleotide of (1) above selected from the group consisting of
(d) a polynucleotide encoding a protein consisting of the amino acid sequence of SEQ ID NO: 2, or encoding an amino acid sequence of SEQ ID NO: 2 wherein 1 to several amino acids thereof is deleted, substituted, inserted, and/or added, and wherein said protein has an acetohydroxy-acid reductoisomerase activity.

(3) The polynucleotide of (1) above consisting of SEQ ID NO: 1.

(4) The polynucleotide of (1) above encoding a protein consisting of SEQ ID NO: 2.

(5) The polynucleotide of any one of (1) to (4) above, wherein the polynucleotide is DNA.

(6) A protein encoded by the polynucleotide of any one of (1) to (5) above.

(7) A vector comprising the polynucleotide of any one of (1) to (5) above.

(7a) The vector of (7) above, which comprises the expression cassette comprising the following components:
(x) a promoter that can be transcribed in a yeast cell;
(y) any of the polynucleotides described in (1) to (5) above linked to the promoter in a sense or antisense direction; and
(z) a signal that can function in a yeast with respect to transcription termination and polyadenylation of a RNA molecule.

(8) A yeast, wherein the vector of (7) above is introduced.

(9) The yeast of (8) above, wherein a capability of producing total vicinal diketones or a capability of producing total diacetyl is reduced by introducing the vector of (7) above.

(10) The yeast of (8) above, wherein a capability of producing total vicinal diketones or a capability of producing total diacetyl is reduced by increasing an expression level of the protein of (6) above.

(11) A method for producing an alcoholic beverage by using the yeast of any one of (8) through (10) above.

(12) The method for producing an alcoholic beverage of (11) above, wherein the brewed alcoholic beverage is a malt beverage.

(13) The method for producing an alcoholic beverage of (11) above, wherein the brewed alcoholic beverage is wine.

(14) An alcoholic beverage produced by the method of any one of (11) through (13) above.

(15) A method for assessing a test yeast for its capability of producing total vicinal diketones or capability of producing total diacetyl, comprising using a primer or a probe designed based on a nucleotide sequence of a acetohydroxy-acid reductoisomerase gene having the nucleotide sequence of SEQ ID NO: 1.

(15a) A method for selecting a yeast having a reduced capability of producing total vicinal diketones or capability of producing total diacetyl by using the method described in (15) above.

(15b) A method for producing an alcoholic beverage (for example, beer) by using the yeast selected with the method described in (15a) above.

(16) A method for assessing a test yeast for its capability of producing total vicinal diketones or capability of producing total diacetyl, comprising: culturing a test yeast; and measuring an expression level of a acetohydroxy-acid reductoisomerase gene having the nucleotide sequence of SEQ ID NO: 1.

(16a) A method for selecting a yeast having a reduced capability of producing total vicinal diketones or capability of producing total diacetyl, which comprises assessing a test yeast by the method described in (16) above and selecting a yeast having a high expression level of acetohydroxy-acid reductoisomerase gene.

(16b) A method for producing an alcoholic beverage (for example, beer) by using the yeast selected with the method in (16a) above.

(17) A method for selecting a yeast, comprising: culturing test yeasts; quantifying the protein of (6) above or measuring an expression level of a acetohydroxy-acid reductoisomerase gene having the nucleotide sequence of SEQ ID NO: 1; and selecting a test yeast having said protein amount or said gene expression level according to a target capability of producing total vicinal diketones or capability of producing total diacetyl.

(17a) A method for selecting a yeast, comprising: culturing test yeasts; quantifying capability of producing total vicinal diketones or capability of producing total diacetyl or activity of an acetohydroxy-acid reductoisomerase; and selecting a test yeast having a target capability of producing total vicinal diketones or capability of producing total diacetyl or activity of acetohydroxy-acid reductoisomerase.

(18) The method for selecting a yeast of (17) above, comprising: culturing a reference yeast and test yeasts; measuring an expression level of a acetohydroxy-acid reductoisomerase gene having the nucleotide sequence of SEQ ID NO: 1 in each yeast; and selecting a test yeast having the gene expressed higher than that in the reference yeast.

(19) The method for selecting a yeast of (17) above comprising: culturing a reference yeast and test yeasts; quantifying the protein of (6) above in each yeast; and selecting a test yeast having said protein for a larger amount than that in the reference yeast.

(20) A method for producing an alcoholic beverage comprising: conducting fermentation for producing an alcoholic beverage using the yeast according to any one of (8) to (10) or a yeast selected by the method according to any one of (17) to (19); and reducing the production amount of total vicinal diketones or the production amount of total diacetyl.

AHB: α-aceto-α-hydroxybutyrate; AL: α-acetolactate; DHMV: α,β-dihydroxy-β-methylvalerate; DHIV: α,β-dihydroxy isovalerate.

Figure 1:
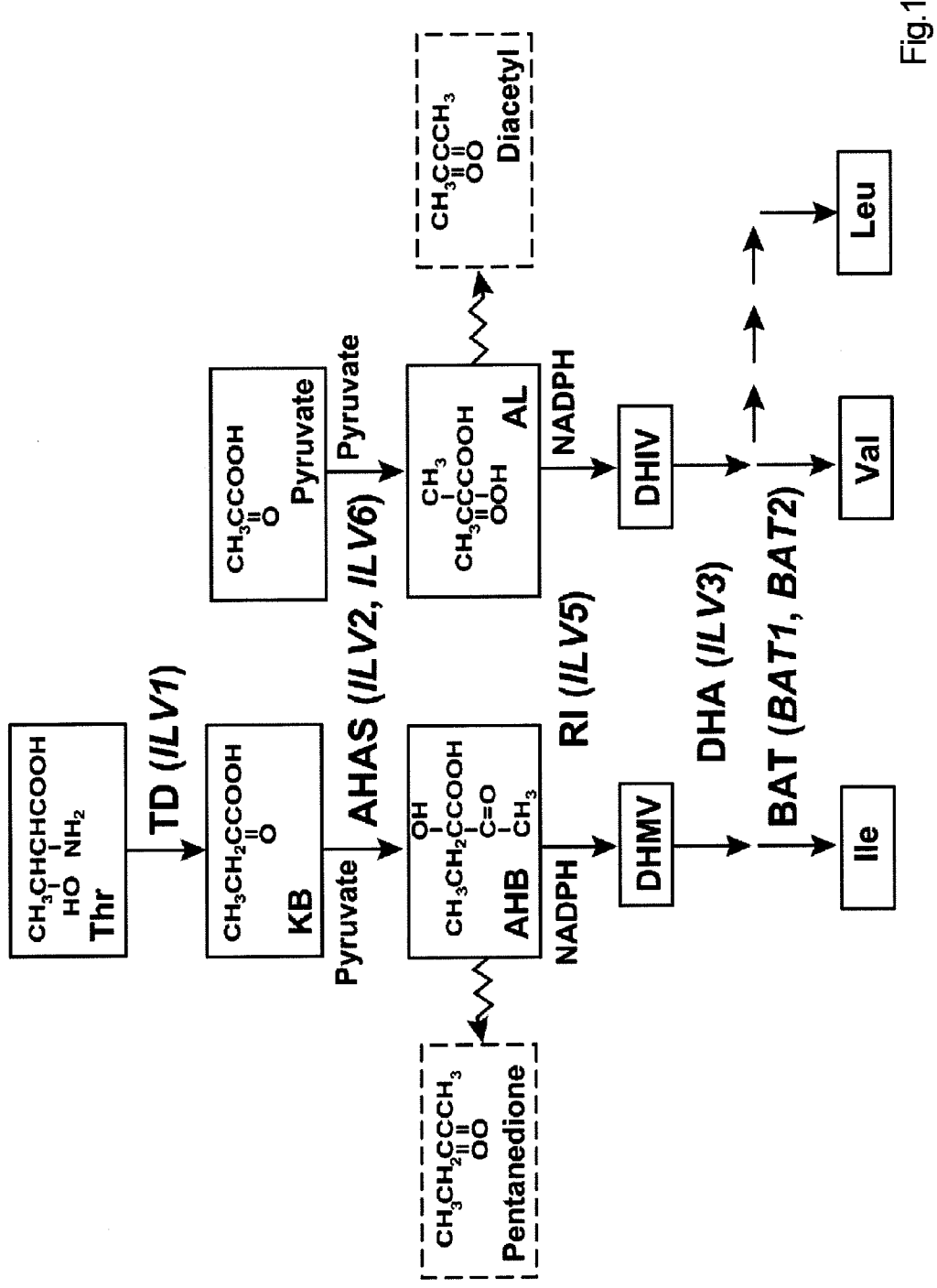
FIG. 1 shows schematic illustration for isoleucine and valine biosynthesis. Five enzymes, acetohydroxyacid synthase (AHAS), acetohydroxyacid reductoisomerase (RI), dihydroxyacid dehydratase (DHA), and branched-chain amino acid aminotransferase/transaminase (BAT) are shared by the two pathways. Corresponding genes are indicated in parenthesis. TD: threonine deaminase; KB: α-ketobutyrate.
Figure 2:
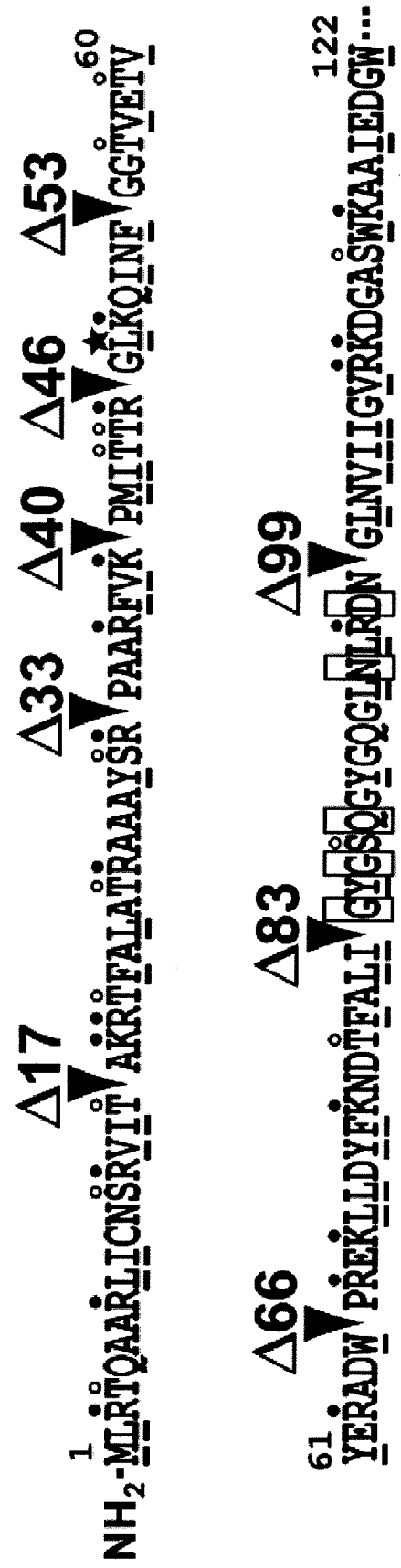

FIG. 2 shows truncations at the N-terminus of Ilv5p precursor protein (SEQ ID NO: 18). Amino acid numbers in Ilv5p precursor protein are shown. The truncation sites of eight mutant proteins are indicated by an arrowhead. The leucine residue at position 48 (the N-terminus of mature Ilv5p) is marked with a star. Basic residues, hydroxylated residues, and hydrophobic residues are shown by a closed dot, an open dot, and an underline, respectively. The boxed residues are conserved amino acids in domain I responsible for NADPH-binding of acetohydroxyacid reductoisomerases (Dumas et al. 1995).

Figure 3:
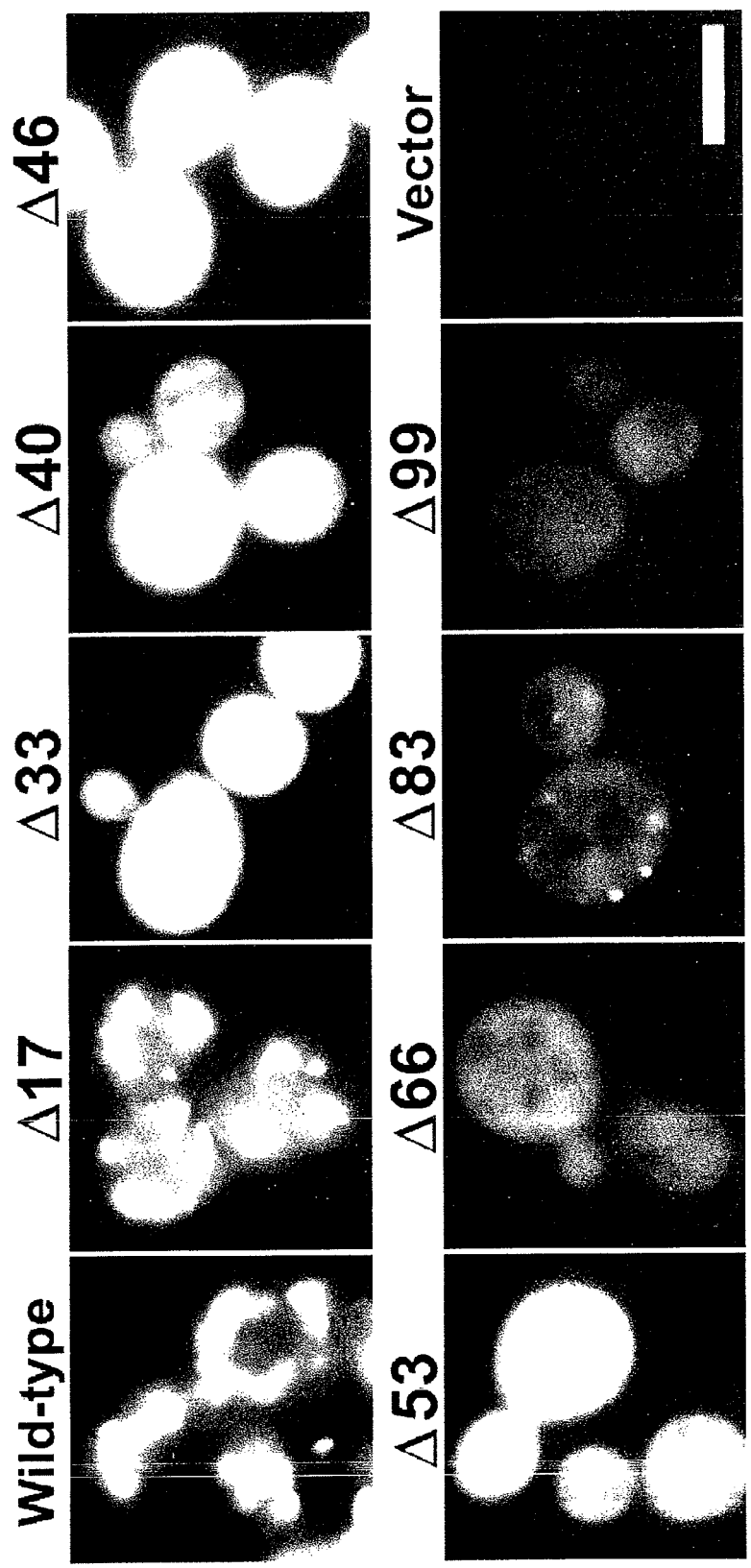

FIG. 3 shows localization of wild-type and N-terminally truncated Ilv5p-GFP fusion constructs in yeast strain M1-2B (Stinchcomb et al. 1980). The numbers of truncated residues are shown. The cells with the control empty vector DNA exhibited no fluorescence. Bar, 5 μm.

Figure 4:
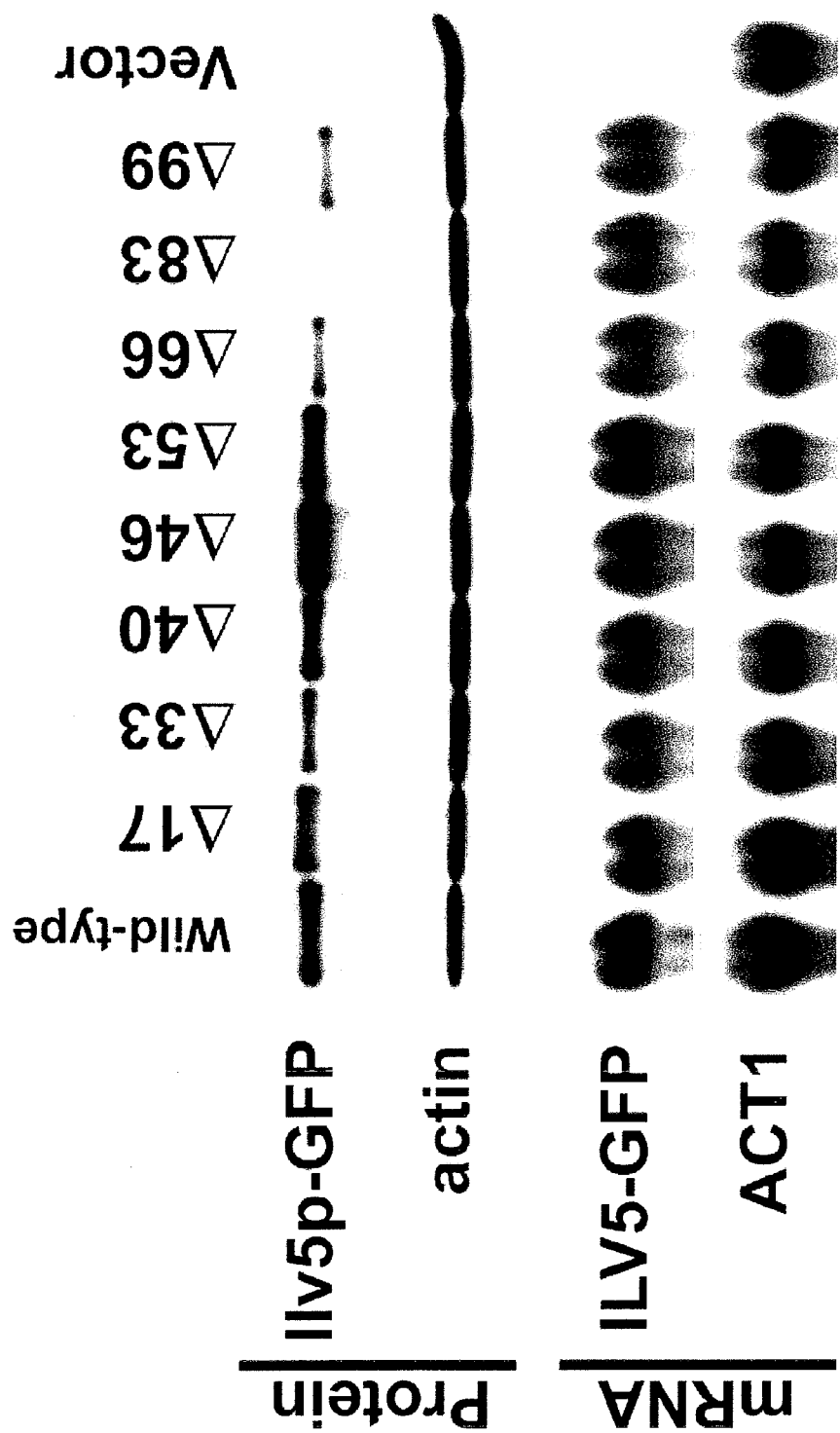

FIG. 4 shows the results of immunoblot analysis for truncated Ilv5p-GFP. Control actin protein in each lysate was used as an internal standard. Total RNA was prepared from the cells grown to logarithmic phase, and processed for Northern analysis using labeled ILV5 and ACT1 ORF DNA fragments as probes.

Figure 5:
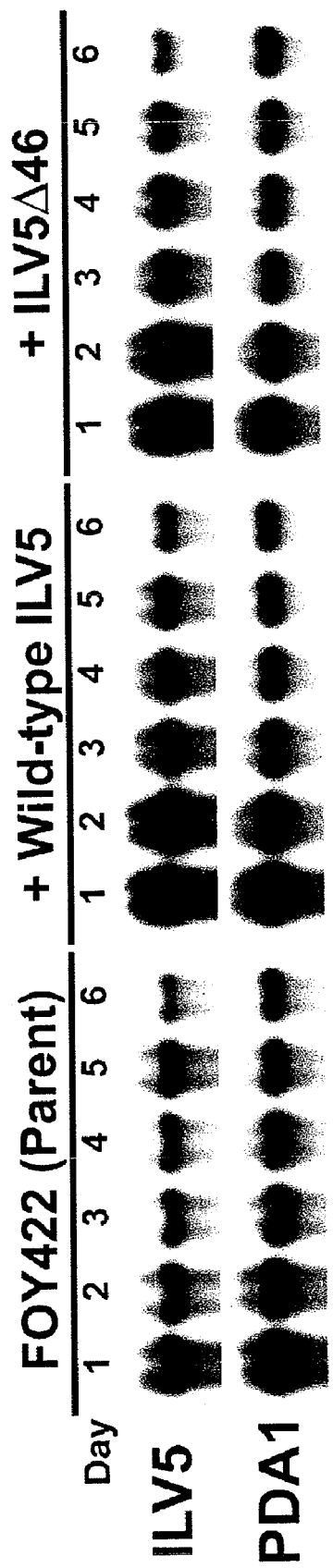

FIG. 5 shows the results of Northern blotting analysis to confirm expression of the wild-type ILV5 gene and the cytoplasmic ILV5Δ46 gene during the beer fermentation. Total RNA was prepared from the samples withdrawn from the fermentation tube once every day, and was analyzed by Northern analysis using labeled ILV5 and PDA1 (Wenzel et al. 1993) ORF fragments as probes.

Figure 6:
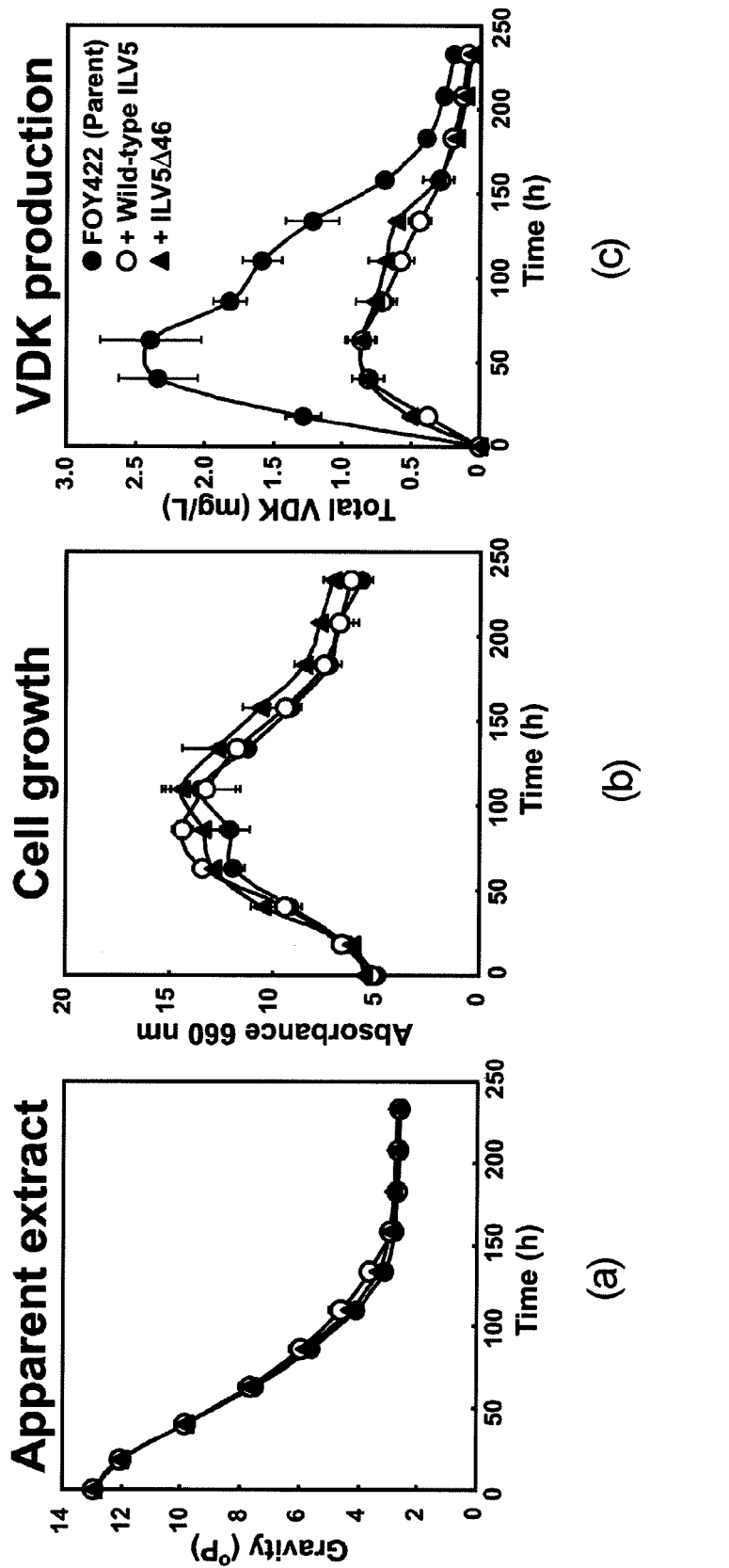

FIG. 6 shows effect of Ilv5p overexpression in lager brewing yeast on beer fermentation performance. FIGS. 6(a), 6(b) and 6(c) shows changes in apparent extract in the wort, cell growth, and the total VDK production, respectively, during the fermentation trial with parental strain FOY422 (●), wild-type Ilv5p-expressing strain FOY437 (○), and Ilv5pΔ46-expressing strain FOY438 (▲). The results are mean values of three independent experiments. Standard deviations are indicated by error bars.

BEST MODES FOR CARRYING OUT THE INVENTION

Vicinal diketones (VDK) are a cause of butter-like beer off-flavor, and are formed by a non-enzymatic oxidative decarboxylation of α-aceto-α-hydroxybutyrate and α-acetolactate, which are intermediates produced in isoleucine and valine biosynthesis taking place in the mitochondria. On an assumption that part of α-acetolactate can be formed also in the cytoplasm due to a mislocalization of the responsible acetohydroxyacid synthase encoded by ILV2 and ILV6 genes, functional expression in the cytoplasm of acetohydroxyacid reductoisomerase (Ilv5p) was explored in order to metabolize the cytoplasmically formed α-aetolatate, whereby the total VDK production was lowered. Among mutant Ilv5p enzymes with a various degree of N-terminal truncation, one with the 46-residue deletion (Ilv5pΔ46) exhibited an unequivocal localization in the cytoplasm judged from microscopy of the Ilv5pΔ46-GFP fusion protein and incapability of Ilv5pΔ46 to complement isoleucine/valine auxotrophy in an ilv5Δ strain. When introduced into an industrial lager brewing strain, a robust expression of Ilv5pΔ46 was as effective as that of a wild-type Ilv5p in lowering the total VDK production in a 2-L scale fermentation trial. Unlike the case of the wild-type Ilv5p, an additional expression of Ilv5pΔ46 did not alter the quality of the resultant beer in terms of contents of aromatic compounds and organic acids. The present invention was completed based on these findings.

1. Polynucleotide of the Invention

First of all, the present invention provides a polynucleotide selected from the group consisting of (a) a polynucleotide consisting of the nucleotide sequence of SEQ ID NO:1; or (b) a polynucleotide encoding a protein consisting of the amino acid sequence of SEQ ID NO:2. The protein consisting of the amino acid sequence of SEQ ID NO:2 is a mutant Ilv5 protein in which N-terminal 46 amino acid residues are deleted (which can be also referred to as Ilv5pΔ46). The nucleotide sequence of SEQ ID NO:1 encodes the amino acid sequence of the Ilv5pΔ46. The polynucleotide can be DNA or RNA.

The target polynucleotide of the present invention is not limited to the above-identified polynucleotides, but include (c) a polynucleotide encoding a protein consisting of the amino acid sequence of SEQ ID NO:2 with one to 15 amino acids thereof being deleted, substituted, inserted and/or added, and having an acetohydroxy-acid reductoisomerase activity, with proviso that the addition and/or deletion does not occur at the N-terminus.

Such proteins include a protein consisting of an amino acid sequence of SEQ ID NO: 2 with, for example, 1 to 15, 1 to 14, 1 to 13, 1 to 12, 1 to 11, 1 to 10, 1 to 9, 1 to 8, 1 to 7, 1 to 6 (1 to several amino acids), 1 to 5, 1 to 4, 1 to 3, 1 to 2, or 1 amino acid residues thereof being deleted, substituted, inserted and/or added and having an acetohydroxy-acid reductoisomerase activity. In general, the number of deletions, substitutions, insertions, and/or additions is preferably smaller. In addition, such proteins include (d) a protein having an amino acid sequence with about 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher identity with the amino acid sequence of SEQ ID NO: 2, and having an acetohydroxy-acid reductoisomerase activity. In general, the percentage identity is preferably higher.

Acetohydroxy-acid reductoisomerase activity may be measured, for example, by a method of Arfin et al. as described in Methods Enzymol., 17: 751-755 (1970).

Furthermore, the present invention may include (d) a polynucleotide comprising a polynucleotide which hybridizes to a polynucleotide consisting of a nucleotide sequence complementary to the nucleotide sequence of SEQ ID NO: 1 under stringent conditions and which encodes a protein having an acetohydroxy-acid reductoisomerase activity; and (f) a polynucleotide comprising a polynucleotide which hybridizes to a polynucleotide complementary to a nucleotide sequence of encoding a protein of SEQ ID NO: 2 under stringent conditions, and which encodes a protein having an acetohydroxy-acid reductoisomerase activity. The polynucleotide encoding a mutant Ilv5 protein in which N-terminal 47 amino acid residues are deleted, should be excluded from the present invention.

Herein, "a polynucleotide that hybridizes under stringent conditions" refers to nucleotide sequence, such as a DNA, obtained by a colony hybridization technique, a plaque hybridization technique, a southern hybridization technique or the like using all or part of polynucleotide of a nucleotide sequence complementary to the nucleotide sequence of SEQ ID NO: 1 or polynucleotide encoding the amino acid sequence of SEQ ID NO: 2 as a probe. The hybridization method may be a method described, for example, in Molecular Cloning 3rd Ed., Current Protocols in Molecular Biology, John Wiley & Sons 1987-1997.

The term "stringent conditions" as used herein may be any of low stringency conditions, moderate stringency conditions or high stringency conditions. "Low stringency conditions" are, for example, 5×SSC, 5×Denhardt's solution, 0.5% SDS, 50% formamide at 32° C. "Moderate stringency conditions" are, for example, 5×SSC, 5×Denhardt's solution, 0.5% SDS, 50% formamide at 42° C. "High stringency conditions" are, for example, 5×SSC, 5×Denhardt's solution, 0.5% SDS, 50% formamide at 50° C. Under these conditions, a polynucleotide, such as a DNA, with higher homology is expected to be obtained efficiently at higher temperature, although multiple factors are involved in hybridization stringency including temperature, probe concentration, probe length, ionic strength, time, salt concentration and others, and one skilled in the art may appropriately select these factors to realize similar stringency.

When a commercially available kit is used for hybridization, for example, Alkphos Direct Labeling Reagents (Amersham Pharmacia) may be used. In this case, according to the attached protocol, after incubation with a labeled probe overnight, the membrane is washed with a primary wash buffer containing 0.1% (w/v) SDS at 55° C., thereby detecting hybridized polynucleotide, such as DNA.

Other polynucleotides that can be hybridized include polynucleotides having about 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher identity to polynucleotide encoding the amino acid sequence of SEQ ID NO: 2 as calculated by homology search software, such as FASTA and BLAST using default parameters.

Identity between amino acid sequences or nucleotide sequences may be determined using algorithm BLAST by Karlin and Altschul (Proc. Natl. Acad. Sci. USA, 87: 2264-2268, 1990; Proc. Natl. Acad. Sci. USA, 90: 5873, 1993). Programs called BLASTN and BLASTX based on BLAST algorithm have been developed (Altschul SF et al., J. Mol. Biol. 215: 403, 1990). When a nucleotide sequence is sequenced using BLASTN, the parameters are, for example, score=100 and word length=12. When an amino acid sequence is sequenced using BLASTX, the parameters are, for example, score=50 and word length=3. When BLAST and Gapped BLAST programs are used, default parameters for each of the programs are employed.

2. Protein of the Present Invention

The present invention also provides proteins encoded by any of the polynucleotides (a) to (d) above. A preferred protein of the present invention comprises an amino acid sequence of SEQ ID NO:2 with one or several amino acids thereof being deleted, substituted, inserted and/or added, and has an acetohydroxy-acid reductoisomerase activity, with proviso that the addition and/or deletion does not occur at the N-terminus.

Such protein includes those having an amino acid sequence of SEQ ID NO: 2 with amino acid residues thereof of the number mentioned above being deleted, substituted, inserted and/or added and having an acetohydroxy-acid reductoisomerase activity. In addition, such protein includes those having homology of about 85% or more, further more preferably about 90% or more, or the most preferably about 95% or more as described above with the amino acid sequence of SEQ ID NO: 2 and having an acetohydroxy-acid reductoisomerase activity.

Such proteins may be obtained by employing site-directed mutation described, for example, in Molecular Cloning 3rd Ed., Current Protocols in Molecular Biology, Nuc. Acids. Res., 10: 6487 (1982), Proc. Natl. Acad. Sci. USA 79: 6409 (1982), Gene 34: 315 (1985), Nuc. Acids. Res., 13: 4431 (1985), Proc. Natl. Acad. Sci. USA 82: 488 (1985).

Deletion, substitution, insertion and/or addition of one or more amino acid residues in an amino acid sequence of the protein of the invention means that one or more amino acid residues are deleted, substituted, inserted and/or added at any one or more positions in the same amino acid sequence. Two or more types of deletion, substitution, insertion and/or addition may occur concurrently.

Hereinafter, examples of mutually substitutable amino acid residues are enumerated. Amino acid residues in the same group are mutually substitutable. The groups are provided below.

Group A: leucine, isoleucine, norleucine, valine, norvaline, alanine, 2-aminobutanoic acid, methionine, o-methylserine, t-butylglycine, t-butylalanine, cyclohexylalanine; Group B: asparatic acid, glutamic acid, isoasparatic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; and Group G: phenylalanine, tyrosine.

The protein of the present invention may also be produced by chemical synthesis methods such as Fmoc method (fluorenylmethyloxycarbonyl method) and tBoc method (t-butyloxycarbonyl method). In addition, peptide synthesizers available from, for example, Advanced ChemTech, PerkinElmer, Pharmacia, Protein Technology Instrument, Synthecell-Vega, PerSeptive, Shimazu Corp. can also be used for chemical synthesis.

3. Vector of the Invention and Yeast Transformed with the Vector

The present invention then provides a vector comprising the polynucleotide described above. The vector of the present invention is directed to a vector including any of the polynucleotides (such as DNA) described in (a) to (d) above. Generally, the vector of the present invention comprises an expression cassette including as components (x) a promoter that can transcribe in a yeast cell; (y) a polynucleotide (such as DNA) described in any of (a) to (i) above that is linked to the promoter in sense or antisense direction; and (z) a signal that functions in the yeast with respect to transcription termination and polyadenylation of RNA molecule.

A vector introduced in the yeast may be any of a multicopy type (YEp type), a single copy type (YCp type), or a chromosome integration type (YIp type). For example, YEp24 (J. R. Broach et al., Experimental Manipulation of Gene Expression, Academic Press, New York, 83, 1983) is known as a YEp type vector, YCp50 (M. D. Rose et al., Gene 60: 237, 1987) is known as a YCp type vector, and YIp5 (K. Struhl et at, Proc. Natl. Acad. Sci. USA, 76: 1035, 1979) is known as a YIp type vector, all of which are readily available.

Promoters/terminators for adjusting gene expression in yeast may be in any combination as long as they function in the brewery yeast and they have no influence on the concentration of constituents such as amino acid and extract in fermentation broth. For example, a promoter of glyceraldehydes 3-phosphate dehydrogenase gene (TDH3), or a promoter of 3-phosphoglycerate kinase gene (PGK1) may be used. These genes have previously been cloned, described in detail, for example, in M. F. Tuite et al., EMBO J., 1, 603 (1982), and are readily available by known methods.

Since an auxotrophy marker cannot be used as a selective marker upon transformation for a brewery yeast, for example, a geneticin-resistant gene (G418r), a copper-resistant gene (CUP1) (Marlin et al., Proc. Natl. Acad. Sci. USA, 81, 337 1984) or a cerulenin-resistant gene (fas2m, PDR4) (Junji Inokoshi et al., Biochemistry, 64, 660, 1992; and Hussain et al., Gene, 101: 149, 1991, respectively) may be used.

A vector constructed as described above is introduced into a host yeast. Examples of the host yeast include any yeast that can be used for brewing, for example, brewery yeasts for beer, wine and sake. Specifically, yeasts such as genus *Saccharomyces* may be used. According to the present invention, a lager brewing yeast, for example, *Saccharomyces pastorianus* W34/70, *Saccharomyces carlsbergensis* NCYC453 or NCYC456, or *Saccharomyces cerevisiae* NBRC1951, NBRC1952, NBRC1953 or NBRC1954 may be used. In addition, wine yeasts such as wine yeasts #1, 3 and 4 from the Brewing Society of Japan, and sake yeasts such as sake yeast #7 and 9 from the Brewing Society of Japan may also be used but not limited thereto. In the present invention, lager brewing yeasts such as *Saccharomyces pastorianus* may be used preferably.

A yeast transformation method may be a generally used known method. For example, methods that can be used include but not limited to an electroporation method (Meth. Enzym., 194: 182 (1990)), a spheroplast method (Proc. Natl. Acad. Sci. USA, 75: 1929 (1978)), a lithium acetate method (J. Bacteriology, 153: 163 (1983)), and methods described in Proc. Natl. Acad. Sci. USA, 75: 1929 (1978), Methods in Yeast Genetics, 2000 Edition: A Cold Spring Harbor Laboratory Course Manual.

More specifically, a host yeast is cultured in a standard yeast nutrition medium (e.g., YEPD medium (Genetic Engineering. Vol. 1, Plenum Press, New York, 117 (1979)), etc.) such that OD600 nm will be 1 to 6. This culture yeast is collected by centrifugation, washed and pre-treated with alkali ion metal ion, preferably lithium ion at a concentration of about 1 to 2 M. After the cell is left to stand at about 30° C. for about 60 minutes, it is left to stand with DNA to be introduced (about 1 to 20 μg) at about 30° C. for about another 60 minutes. Polyethyleneglycol, preferably about 4,000 Dalton of polyethyleneglycol, is added to a final concentration of about 20% to 50%. After leaving at about 30° C. for about 30 minutes, the cell is heated at about 42° C. for about 5 minutes. Preferably, this cell suspension is washed with a standard yeast nutrition medium, added to a predetermined amount of fresh standard yeast nutrition medium and left to stand at about 30° C. for about 60 minutes. Thereafter, it is seeded to a standard agar medium containing an antibiotic or the like as a selective marker to obtain a transformant.

Other general cloning techniques may be found, for example, in Molecular Cloning 3rd Ed., and Methods in Yeast Genetics, A Laboratory Manual (Cold Spring Harbor Laboratory Press, Cold Spring Harbor, N.Y.).

4. Method of Producing Alcoholic Beverages According to the Present Invention and Alcoholic Beverages Produced by the Method The vector of the present invention described above is introduced into a yeast suitable for brewing a target alcoholic product. This yeast can be used to reduce the level of VDKs, especially DA, of desired alcoholic beverages, and produce alcoholic beverages having enhanced flavor. In addition, yeasts to be selected by the yeast assessment method of the present invention can also be used. The target alcoholic beverages include, for example, but not limited to beer, sparkling liquor (*happoushu*) such as a beer-taste beverage, wine, whisky, sake and the like.

In order to produce these alcoholic beverages, a known technique can be used except that a brewery yeast obtained according to the present invention is used in the place of a parent strain. Since materials, manufacturing equipment, manufacturing control and the like may be exactly the same as the conventional ones, there is no need of increasing the cost for producing alcoholic beverages with an decreased level of VDKs, especially DA. Thus, according to the present invention, alcoholic beverages with enhanced flavor can be produced using the existing facility without increasing the cost.

5. Yeast Assessment Method of the Invention

The present invention relates to a method for assessing a test yeast for its capability of producing total vicinal diketones or capability of producing total diacetyl by using a primer or a probe designed based on a nucleotide sequence of a acetohydroxy-acid reductoisomerase gene having the nucleotide sequence of SEQ ID NO:1. General techniques for such assessment method is known and is described in, for example, WO01/040514, Japanese Laid-Open Patent Application No. 8-205900 or the like. This assessment method is described in below.

First, genome of a test yeast is prepared. For this preparation, any known method such as Hereford method or potassium acetate method may be used (e.g., Methods in Yeast Genetics, Cold Spring Harbor Laboratory Press, 130 (1990)). Using a primer or a probe designed based on a nucleotide sequence (preferably, ORF sequence) of the acetohydroxy-acid reductoisomerase gene, the existence of the gene or a sequence specific to the gene is determined in the test yeast genome obtained. The primer or the probe may be designed according to a known technique.

Detection of the gene or the specific sequence may be carried out by employing a known technique. For example, a polynucleotide including part or all of the specific sequence or a polynucleotide including a nucleotide sequence complementary to said nucleotide sequence is used as one primer, while a polynucleotide including part or all of the sequence upstream or downstream from this sequence or a polynucleotide including a nucleotide sequence complementary to said nucleotide sequence, is used as another primer to amplify a nucleic acid of the yeast by a PCR method, thereby determining the existence of amplified products and molecular weight of the amplified products. The number of bases of polynucleotide used for a primer is generally 10 base pairs (bp) or more, and preferably 15 to 25 bp. In general, the number of bases between the primers is suitably 300 to 2000 bp.

The reaction conditions for PCR are not particularly limited but may be, for example, a denaturation temperature of 90 to 95° C., an annealing temperature of 40 to 60° C., an elongation temperature of 60 to 75° C., and the number of cycle of 10 or more. The resulting reaction product may be separated, for example, by electrophoresis using agarose gel to determine the molecular weight of the amplified product. This method allows prediction and assessment of the capability of producing total vicinal diketones or capability of producing total diacetyl of the yeast as determined by whether the molecular weight of the amplified product is a size that contains the DNA molecule of the specific part. In addition, by analyzing the nucleotide sequence of the amplified product, the capability may be predicted and/or assessed more precisely.

Moreover, in the present invention, a test yeast is cultured to measure an expression level of the acetohydroxy-acid reductoisomerase gene having the nucleotide sequence of SEQ ID NO: 1 to assess the test yeast for its capability of producing total vicinal diketones or capability of producing total diacetyl. In this case, the test yeast is cultured and then mRNA or a protein resulting from the acetohydroxy-acid reductoisomerase gene is quantified. The quantification of mRNA or protein may be carried out by employing a known technique. For example, mRNA may be quantified, by Northern hybridization or quantitative RT-PCR, while protein may be quantified, for example, by Western blotting (Current Protocols in Molecular Biology, John Wiley & Sons 1994-2003).

Furthermore, test yeasts are cultured and expression levels of the gene of the present invention having the nucleotide sequence of SEQ ID NO: 1 are measured to select a test yeast with the gene expression level according to the target capability of producing total vicinal diketones or capability of producing total diacetyl, thereby selecting a yeast favorable for brewing desired alcoholic beverages. In addition, a reference yeast and a test yeast may be cultured so as to measure and compare the expression level of the gene in each of the yeasts, thereby selecting a favorable test yeast. More specifically, for example, a reference yeast and one or more test yeasts are cultured and an expression level of the acetohydroxy-acid reductoisomerase gene having the nucleotide sequence of SEQ ID NO: 1 is measured in each yeast. By selecting a test yeast with the gene expressed higher than that in the reference yeast, a yeast suitable for brewing alcoholic beverages can be selected.

Alternatively, test yeasts are cultured and a yeast with a lower capability of producing total vicinal diketones or capability of producing total diacetyl, or a higher activity of acetohydroxy-acid reductoisomerase is selected, thereby selecting a yeast suitable for brewing desired alcoholic beverages.

In these cases, the test yeasts or the reference yeast may be, for example, a yeast introduced with the vector of the invention, a yeast with amplified expression of the gene of the present invention described above, a yeast with amplified expression of the protein of the present invention described above, an artificially mutated yeast or a naturally mutated yeast. Total amount of vicinal diketones may be quantified by a method described in Drews et al., Mon. fur Brau., 34, 1966. Total amount of diacetyl may be quantified by a method, for example, described in J. Agric. Food Chem. 50(13):3647-53, 2002. Acetohydroxy-acid reductoisomerase activity may be measured, for example, by a method of Arfin et al. as described in Methods Enzymol., 17: 751-755 (1970). The mutation treatment may employ any methods including, for example, physical methods such as ultraviolet irradiation and radiation irradiation, and chemical methods associated with treatments with drugs such as EMS (ethylmethane sulphonate) and N-methyl-N-nitrosoguanidine (see, e.g., Yasuji Oshima Ed., Biochemistry Experiments vol. 39, Yeast Molecular Genetic Experiments, pp. 67-75, JSSP).

In addition, examples of yeasts used as the reference yeast or the test yeasts include any yeasts that can be used for brewing, for example, brewery yeasts for beer, wine, sake and the like. More specifically, yeasts such as genus *Saccharomyces* may be used (e.g., *S. pastorianus, S. cerevisiae*, and *S. carlsbergensis*). According to the present invention, a lager brewing yeast, for example, *Saccharomyces pastorianus* W34/70; *Saccharomyces carlsbergensis* NCYC453 or NCYC456; or *Saccharomyces cerevisiae* NBRC1951, NBRC1952, NBRC1953 or NBRC1954 may be used. Further, whisky yeasts such as *Saccharomyces cerevisiae* NCYC90; wine yeasts such as wine yeasts #1, 3 and 4 from the Brewing Society of Japan; and sake yeasts such as sake yeast #7 and 9 from the Brewing Society of Japan may also be used but not limited thereto. In the present invention, lager brewing yeasts such as *Saccharomyces pastorianus* may preferably be used. The reference yeast and the test yeasts may be selected from the above yeasts in any combination.

EXAMPLES

Hereinafter, the present invention will be described in more detail with reference to working examples. The present invention, however, is not limited to the examples described below.

Example 1

Preparation of Plasmids Comprising Cytoplasmic Ilv5p

Plasmids to express mutant Ilv5p-GFP fusion proteins wherein a certain number (17, 33, 40, 46, 53, 66, 83 or 99) of N-terminal amino acid residues are deleted, were prepared in the following manner. Restriction enzyme digests and ligations were carried out using standard methods (Sambrook et al. 1989). Polymerase chain reaction (PCR) products were cloned and sequenced using a TOPO™ TA cloning kit (Invitrogen, Carlsbad, Calif.). The oligonucleotides used in this example are described below.

| Reference Number | Sequence | |
|---|---|---|
| 1 | 5'-gagctcATGTTGAGAACTCAAGCCGCCAGATTGATCTGCA-3' | (SEQ ID NO: 3) |
| 2 | 5'-TTGGTTTTCTGGTCTCAACTTTCTGACTTCCTTA-3' | (SEQ ID NO: 4) |
| 3 | 5'-CAGAAAGTTGAGACCAGAAAACCAAATGAGTAAAGGAGAAGAACT-3' | (SEQ ID NO: 5) |
| 4 | 5'-ggatccCAGTGTGATGGATATCTGCAGAATTCCCGGGGTACCTTATTTGT-3' | (SEQ ID NO: 6) |
| 5 | 5'-gagctcATGGCTAAGAGAACCTTTGCTTTGGCCACC-3' | (SEQ ID NO: 7) |
| 6 | 5'-gagctcATGCCAGCTGCCCGTTTCGTTAAGCCAATG-3' | (SEQ ID NO: 8) |
| 7 | 5'-gagctcATGCCAATGATCACTACCCGTGGTTTGAAG-3' | (SEQ ID NO: 9) |
| 8 | 5'-gagctcATGGGTTTGAAGCAAATCAACTTCGGTGGT-3' | (SEQ ID NO: 10) |
| 9 | 5'-gagctcATGGGTGGTACTGTTGAAACCGTCTACGAA-3' | (SEQ ID NO: 11) |
| 10 | 5'-gagctcATGCCAAGAGAAAAGTTGTTGGACTACTTC-3' | (SEQ ID NO: 12) |

-continued

| Reference Number | Sequence | |
|---|---|---|
| 11 | 5'-gagctcATGGGTTACGGTTCCCAAGGTTACGGTCAA-3' | (SEQ ID NO: 13) |
| 12 | 5'-gagctcATGGGTTTGAACGTTATCATTGGTGTCCGT-3' | (SEQ ID NO: 14) |
| 13 | 5'-TaccggtGACATCGTTCCAGACGGCGT-3' | (SEQ ID NO: 15) |
| 14 | 5'-accggtAAGG CTCACGAAAA GGCCCAAGCT-3' | (SEQ ID NO: 16) |
| 15 | 5'-gtcgacTTAT TGGTTTTCTG GTCTCAACTT-3' | (SEQ ID NO: 17) |

(Note)
The lowercase nucleotides provide restriction sites.
The underlined nucleotides correspond to the extra initiation codon added to the truncated ILV5 N-termini.

The 1.2-kb DNA fragment corresponding to the ILV5 open reading frame (ORF) with an SacI restriction site at the 5'-end was prepared by PCR using oligonucleotides 1+2 as primers with the chromosomal DNA of *Saccharomyces cerevisiae* (strain X2180-1A) as the template. The oligonucleotide 3 contains the ILV5 ORF 3'-end (25 bases) and green fluorescent protein (GFP) ORF 5'-end (20 bases) sequences fused in frame. The 840-bp fragment encoding GFP was amplified using oligonucleotides 3+4 as primers and plasmid pYES-GFP (Omura et al. 2001) as the template. The above two PCR products were mixed and used as the overlapping templates for the subsequent PCR with oligonucleotides 1+4 to give a 2.0-kb ILV5-GFP fusion gene fragment.

The DNA fragment was digested with SacI and BamHI and subcloned into the SacI-BamHI gap of a centromeric yeast expression vector pYCGPY (Kodama et al. 2001) to give pYC-ILV5-GFP.

The DNA fragments for a set of nested deletions in the Ilv5p N-terminus were obtained by PCR using one of the oligonucleotides 5, 6, 7, 8, 9, 10, 11, and 12 (corresponding to the N-terminal deletions Δ17, Δ33, Δ40, Δ46, Δ53, Δ66, Δ83, and Δ99 in FIG. 2) as a forward primer in combination with a reverse primer (the oligonucleotide 13) and the plasmid pYC-ILV5-GFP as the template.

The obtained fragments (ranging from 370-bp to 620-bp) were digested with SacI and AgeI, and substituted for the wild-type SacI-AgeI sequence in the ILV5-GFP construct by ligation with the SacI-AgeI gap of pYC-ILV5-GFP to give eight plasmids, i.e., pYC-ILV5Δ17-GFP, pYC-ILV5Δ33-GFP, pYC-ILV5Δ40-GFP, pYC-ILV5Δ46-GFP, pYC-ILV5Δ53-GFP, pYC-ILV5Δ66-GFP, pYC-ILV5Δ83-GFP and pYC-ILV5Δ99-GFP. The N-terminal deletion Ilv5p-GFP has a methionine initiation codon (ATG) necessary for initiating translation at the N-terminus.

Example 2

Preparation of Transformant/Localization and Stability Study

*S. cerevisiae* strain M1-2B (Stinchcomb et al. 1980) was transformed with pYC-ILV5-GFP (for wild-type fusion protein) and its derivative pYC-ILV5Δx-GFP (where x represents the number of the deleted N-terminal residues of each construct). The transformant cells were grown in YPD supplemented with 300 µg/ml neomycin analogue G418 to logarithmic phase, and were subjected to fluorescence microscopy. Cells were visualized with a fluorescence microscope (model Eclipse E600, Nikon, Tokyo, Japan), and images were taken at 100× using a color chilled 3CCD camera (model C5810, Hamamatsu Photonics, Shizuoka, Japan). The results are as shown in FIG. 3.

As shown in FIG. 3, the Ilv5pΔ17-GFP exhibited a localization pattern similar to that of wild-type Ilv5p-GFP, whereas mutant fusion proteins Ilv5Δ33-GFP, Ilv5pΔ40-GFP, Ilv5pΔ46-GFP, and Ilv5pΔ53-GFP showed an intense fluorescence throughout the cytoplasm, suggesting that the latter four fusion proteins predominantly localize in the cytoplasm rather than the mitochondria. On the other hand, the fusion proteins with a larger deletion Ilv5pΔ66-GFP, Ilv5pΔ83-GFP, and Ilv5pΔ99-GFP gave weaker cytoplasmic fluorescence compared to the other constructs, suggesting that these proteins cannot stably exist in the cytoplasm.

Next, whole cell extracts for sodium dodecyl sulfate-polyacrylamide gel electrophoresis (SDS-PAGE) were prepared as described by Brondijk (1998), and the protein concentration was determined following the method of Bradford using a protein assay kit (Bio-Rad Laboratories, Hercules, Calif.). Sixty µg of the protein were subjected to the SDS-PAGE, and the subsequent immunoblot analysis using a chemiluminescence detection system as described previously (Omura et al. 2001). For antigen detection, rabbit antibody against GFP (Medical and Biological Laboratories, Nagoya, Japan) and rabbit antibody against actin (Santa Cruz Biotechnology, Santa Cruz, Calif.) were used at 1:1000 dilution. As internal standard of the cell extracts, actin level was detected with anti-actin antibody. The results are as shown in FIG. 4.

As shown in FIG. 4, among the N-terminal truncated Ilv5p-GFP fusion proteins tested, the amount of Ilv5p-GFPΔ46 in a predetermined amount of the cell extracts was highest, with the amount of Ilv5p-GFPΔ53 and Ilv5p-GFPΔ40 being higher in this order. Accordingly, it was found that deletion of N-terminal 46 amino acid residues is most suitable when preparing cytoplasmic Ilv5p.

Example 3

Beer Fermentation Trial

Wilde-type Ilv5p or cytoplasmic Ilv5p (mutant Ilv5pΔ46 in which N-terminal 46 amino acid residues are deleted) were introduced into a lager brewing yeast to construct expression plasmids for stable expression. In order to prepare an ILV5 ORF with a stop codon at the 3'-end, PCR was performed with the oligonucleotides 14+15 as primers and plasmid pYC-ILV5-GFP as the template. The obtained 530-bp fragment was digested with AgeI and SalI, and ligated into the SacI-SalI gap of an integrative expression vector pUP3GLP (Omura et al. 2001) together with one of the SacI-AgeI fragments excised from pYC-ILV5-GFP (670-bp) and pYI-ILV5Δ46 (540-bp), respectively. The expression plasmids were designated as pYI-ILV5 and pYI-ILV5Δ46, respectively, and introduced into lager brewing yeast FOY422 (high VDK-producing strain derived from J strain (obtained from Versuchs- and Lehrenstalt für Brauerei, Berlin). The strains were designated as FOY437 (comprising wilde-type Ilv5p) and FOY438 (comprising cytoplasmic Ilv5p Δ46), and subjected to the following fermentation trial. The beer fermentation trial was conducted under the following conditions.

| Trial Scale: | 2-liter tall tube |
|---|---|
| Wort: | 100% malt wort (hop added) |
| Initial Wort Gravity: | 12.9° Plato (1° P corresponds to the gravity of 1% w/w sucrose solution) |
| Pitching Rate: | $1.5 \times 10^7$ cells/mL |
| Wort extract concentration: | 11.85% |
| Wort dissolved oxygen concentration: | 8.0 mg/L |
| Fermentation temperature: | 15° C. |

In order to confirm expression of wild-type ILV5 gene and cytoplasmic ILV5 Δ46 gene, the yeasts were collected from the fermentation broth 1, 2, 3, 4, 5 and 6 days after the initiation of the fermentation. Isolation of total RNA and subsequent agarose gel electrophoresis and blotting were carried out according to standard methods (Rose et al. 1990). In the procedures, 40 μg of the RNA were developed by agarose gel electrophoresis and subjected to northern blotting analysis. mRNA was detected with a probe comprising labeled ILV5 ORF sequence. The results are as shown in FIG. 5. The expression level of PDA1 gene as control was also shown in FIG. 5.

As shown in FIG. 5, as compared to the parental strain, FOY422, the wilde-type ILV5 strain and cytoplasmic ILV5Δ46 strain overexpressed the gene introduced by constitutive promoter TDH3p contained in the expression plasmids. In particular, the difference from the parental strain (control) for the first day and the second day was remarkable.

The sugar attenuation rate and cell growth rate during the fermentation were not adversely affected by introduction of the wilde-type ILV5 gene and cytoplasmic ILV5Δ46 gene. FIGS. 6(a), 6(b) and 6(c) shows changes in apparent extract in the wort, cell growth, and the total VDK production, respectively The yeast growth rate was determined by measuring floating yeast level by absorbance at 660 nm. The VDK level was quantified as "Total VDK" which is the total amount of VDK and its precursors in accordance with a method described in Drews, et al (1966).

As shown in FIG. 6, the total VDK level reached to the peak on the third day from the initiation of fermentation. Although the total VDK level in the FOY 422 strain reached 2.4 mg/L, that in the wilde-type ILV5 strain and that in the cytoplasmic ILV5pΔ46 strain were both reduced to 0.9 mg/L. Further, as compared to the control parental strain, both transformants ended up with an earlier extinction of VDK value below the threshold level (i.e. 0.15 mg/L for diacetyl).

Next, chemical analysis of the beers fermented was carried out. Table 1 shows the results from chemical analysis of the beers fermented for ten days with the parental strain (FOY422) and the transformant strains overexpressing wild-type Ilv5p (FOY437) or Ilv5pΔ46 (FOY438).

TABLE 1

Analysis of beer after the primary fermentation

|  | FOY422 (Parent) | FOY437 (Wild-type ILV5) | FOY438 (ILV5Δ46) |
|---|---|---|---|
| Ethanol (g l$^{-1}$) | 44.5 ± 0.15 | 44.7 ± 0.25 | 44.1 ± 0.30 |
| Glycerol (g l$^{-1}$) | 1.8 ± 0.02 | 1.6 ± 0.03 | 1.8 ± 0.01 |
| Free amino nitrogen (mg l$^{-1}$) | 155 ± 0.3 | 145 ± 1.8 | 148 ± 3.0 |
| Ammonia (mg l$^{-1}$) | 35.3 ± 0.6 | 37.5 ± 1.3 | 31.0 ± 1.2 |
| Sulfite (mg l$^{-1}$) | 12.5 ± 0.32 | 9.3 ± 0.66 | 9.1 ± 1.26 |
| Acetaldehyde (mg l$^{-1}$) | 0.9 ± 0.18 | 0.9 ± 0.18 | 0.8 ± 0.06 |
| Organic acids |  |  |  |
| Citrate (mg l$^{-1}$) | 303 ± 6.7 | 312 ± 2.5 | 313 ± 1.3 |
| Pyruvate (mg l$^{-1}$) | 152 ± 1.9 | 91.2 ± 6.1 | 176 ± 1.8 |
| Malate (mg l$^{-1}$) | 171 ± 2.1 | 177 ± 2.3 | 166 ± 0.8 |
| Succinate (mg l$^{-1}$) | 99.1 ± 0.8 | 101 ± 0.4 | 98.3 ± 1.5 |
| Lactate (g l$^{-1}$) | 316 ± 9.9 | 324 ± 8.4 | 336 ± 6.6 |
| Acetate (mg l$^{-1}$) | 181 ± 2.6 | 133 ± 3.5 | 170 ± 2.3 |
| Fusel alcohols |  |  |  |
| Propyl alcohol (mg l$^{-1}$) | 11.1 ± 0.3 | 12.6 ± 0.1 | 11.1 ± 0.4 |
| Isobutyl alcohol (mg l$^{-1}$) | 9.7 ± 0.6 | 13.1 ± 0.2 | 8.9 ± 0.7 |
| Amyl alcohols (mg l$^{-1}$) | 46.9 ± 1.7 | 57.9 ± 0.8 | 43.8 ± 2.6 |
| Esters |  |  |  |
| Ethyl acetate (mg l$^{-1}$) | 34.2 ± 0.2 | 38.1 ± 0.1 | 34.8 ± 0.5 |
| Isoamyl acetate (mg l$^{-1}$) | 1.20 ± 0.02 | 1.72 ± 0.01 | 1.09 ± 0.06 |

All the results shown are mean values of three independent experiments including standard deviations.

The quality of beer with FOY438 was indistinguishable from the beer with the parental strain. On the other hand, the beer from FOY437 with overexpression of the wild-type Ilv5p appeared to have some different characteristics compared to the beer with the parental strain: e.g. smaller amounts of pyruvate (60% of the control beer with FOY422) and acetate (73%), and larger amounts of isobutyl alcohol (135%), amylalcohols (123%), and isoamyl acetate (143%).

From the results of these experiments, it was found that high expression of cytoplasmic Ilv5pΔ46 can reduce VDK level without impairing beer quality.

INDUSTRIAL APPLICABILITY

According to the method for producing alcoholic beverages of the present invention, because of reduction of the production amount of VDKs, especially DA, which are responsible for off-flavors in products, alcoholic beverages with superior flavor can be produced.

The References Cited in this Application are as Follows.
1. Arfin S M, Bradshaw R A (1988). Biochemistry 27:7979-7984
2. Bateman J M, Perlman P S, Butow R A (2002), Genetics 161:1043-1052
3. Brondijk T H, van der Rest M E, Pluim D, de Vries Y, Stingl K, Poolman B, Konings W N (1998), J Biol Chem 273: 15352-15357
4. De Virgilio C, Bürckert N, Barth G, Neuhaus J M, Boller T, Wiemken A (1992), Yeast 12:1043-1051
5. Dickinson J R, Harrison S J, Hewlins M J E (1998), J Biol Chem 273:25751-25756
6. Dickinson J R, Harrison S J, Dickinson J A, Hewlins M J E (2000), J Biol Chem 275:10937-10942
7. Dillemans M, Goossens E, Goffin O, Masschelein C A (1987), J Am Soc Brew Chem 45:81-84
8. Drews B, Specht H, Bärwald G, Trénel G (1966), Monatsschrift Brauerei 19:34-36
9. Dumas R, Butikofer M-C, Job D, Douce R (1995), Biochemistry 34:6026-6036
10. Endo T, Yamamoto H, Esaki M (2003), J Cell Sci 116: 3259-3267

11. Ernandes J R, Williams J W, Russell I, Stewart G G (1993) Respiratory deficiency in brewing yeast strains: Effects on fermentation, flocculation, and beer flavor components. J Am Soc Brew Chem 51:16-20
12. Fujiwara D, Kobayashi O, Yoshimoto H, Harashima S, Tamai Y (1999), Yeast 15:1183-1197
13. Furukubo S, Shobayashi M, Fukui N, Isoe A, Nakatani K (1993), Tech Q Master Brew Assoc Am 30:155-158
14. Gakh O, Cavadini P, Isaya G (2002), Biochim Biophys Acta 1592:63-77
15. Gjermansen C, Nilsson-Tillgren T, Petersen J G L, Kielland-Brandt M C, Sigsgaard P, Holmberg S (1988), J Basic Microbiol 28:175-183
16. Kassow A (1992), Metabolic effects of deleting the region encoding the transit peptide in Saccharomyces cerevisiae ILV5. PhD thesis, University of Copenhagen
17. Kodama Y, Omura F, Ashikari T (2001), Appl Environ Microbiol 67:3455-3462
18. Kodama Y, Kielland-Brandt M C, Hansen J (2006), In: Sunnerhagen P, Piškur J (eds) Topics in current genetics Vol. 15. Springer, Berlin/Heidelberg, pp 145-164
19. Koehler C M (2004), Annu Rev Cell Dev Biol 20:309-335
20. Lévy F, Johnston J A, Varshaysky A (1999), Eur J Biochem 259:244-252
21. Li X, Chang Y H (1995), Proc Natl Acad Sci USA 92:12357-12361
22. MacAlpine D M, Perlman P S, Butow R A (2000), EMBO J 19:767-775
23. Meilgaard M C (1975), Tech Q Master Brew Assoc Am 12:151-168
24. Nakatani K, Fukui N, Nagami K, Nishigaki M (1991), J Am Soc Brew Chem 49:152-157
25. Omura F, Kodama Y, Ashikari T (2001), FEMS Microbiol Lett 194:207-214
26. Pang S S, Duggleby R G (1999), Biochemistry. 38:5222-5231
27. Petersen J G L, Holmberg S (1986), Nucleic Acids Res 14:9631-9651
28. Polevoda B, Panciera Y, Brown S P, Wei J, Sherman F (2006), Yeast 23:127-139
29. Pronk J T, Steensma H Y, Van Dijken J P (1996), Yeast 16:1607-1633
30. Poulsen C, Stougaard P (1989), Eur J Biochem 185:433-439
31. Rankine B (1962), Aust Wine Brew & Spirit Rev 80:14-16
32. Rose M D, Winston F, Hieter P (1990), a laboratory course manual. Cold Spring Harbor Laboratory Press, New York
33. Ryan E D, Kohlhaw G B (1974), J Bacteriol 120:631-637
34. Sambrook J, Fritsch E F, Maniatis T (1989), Molecular cloning, a laboratory manual, 2nd edn. Cold Spring Harbor Laboratory Press, New York
35. Stinchcomb D T, Thomas M, Kelly J, Selker E, Davis R W (1980), Proc Natl Acad Sci USA 77:4559-4563
36. Suzuki T, Varshaysky A (1999), EMBO J 18:6017-6026
37. Truscott K N, Brandner K, Pfanner N (2003), Curr Biol 13:R326-R337
38. Vakeria D, Box W G, Hinchliffe E (1991), In: Proceedings of the "European Brewery Convention the 23rd congress", 12-16 May, Lisbon, Portugal
39. Varshaysky A (1996), Proc Natl Acad Sci USA 93:12142-12149
40. von Heijne G, Steppuhn J, Herrmann R G (1989), Eur J Biochem 180:535-545
41. Wenzel T J, Luttik M A, van den Berg J A, Steensma H Y (1993), Eur J Biochem 218:405-411
42. Wiedemann N, Kozjak V, Chacinska A, Schönfisch B, Rospert S, Ryan M T, Pfanner N, Meisinger C (2003), Nature 424:565-571
43. Zahedi R P, Sickmann A, Boehm A M, Winkler C, Zufall N, Schönfisch B, Guiard B, Pfanner N, Meisinger C (2006), Mol Biol Cell 17:1436-1450
44. Zelenaya-Troitskaya O, Perlman P S, Butow R A (1995), EMBO J 14:3268-3276

The invention claimed is:

1. An isolated polynucleotide comprising
a polynucleotide encoding a protein consisting of the amino acid sequence of SEQ ID NO:2.

2. The polynucleotide of claim 1, wherein the polynucleotide consists of the nucleotide sequence of SEQ ID NO: 1.

3. The polynucleotide of claim 1, wherein the polynucleotide is DNA.

4. A protein encoded by the polynucleotide of claim 1.

5. A vector comprising the polynucleotide of claim 1.

6. A yeast comprising the vector of claim 5.

7. A yeast comprising a vector comprising the polynucleotide of claim 1, wherein a capability of producing total vicinal diketones or a capability of producing total diacetyl is reduced by introducing the vector comprising the polynucleotide of claim 1.

8. A yeast comprising a vector comprising the polynucleotide of claim 1, wherein a capability of producing total vicinal diketones or a capability of producing total diacetyl is reduced by increasing the expression level of a protein encoded by the polynucleotide of claim 1.

9. A method for producing an alcoholic beverage comprising culturing the yeast of claim 6.

10. The method for producing an alcoholic beverage of claim 9, wherein the brewed alcoholic beverage is a malt beverage.

11. The method for producing an alcoholic beverage of claim 9, wherein the brewed alcoholic beverage is wine.

12. An alcoholic beverage produced by the method of claim 9.

* * * * *